United States Patent [19]

Brenzel

[11] 4,176,136
[45] Nov. 27, 1979

[54] PROCESS FOR PREPARING ETHYLIDENE-BIS-ACETAMIDE

[75] Inventor: Daniel J. Brenzel, Menlo Park, Calif.

[73] Assignee: Dynapol, Palo Alto, Calif.

[21] Appl. No.: 801,485

[22] Filed: May 31, 1977

[51] Int. Cl.$^2$ .......................................... C07C 102/00
[52] U.S. Cl. ............................................... 260/561 R
[58] Field of Search ..................................... 260/561 R

[56] References Cited

U.S. PATENT DOCUMENTS

| | | | |
|---|---|---|---|
| 3,803,091 | 4/1974 | Murfin | 260/561 R |
| 4,018,826 | 4/1977 | Gless et al. | 260/561 R |

OTHER PUBLICATIONS

Kirk-Othmer Encyclopedia of Chemical Technology, 2nd Ed., vol. 11, p. 891.

Primary Examiner—Arthur P. Demers
Attorney, Agent, or Firm—William H. Benz

[57] ABSTRACT

Ethylidene-bis-acetamide is prepared by the process of contacting a liquid mixture of acetaldehyde and acetamide with a solid cation exchange resin at a temperature of from about 10° C. to about 110° C. The ethylidene-bis-acetamide may later be converted to vinylacetamide, a material useful as a monomer for preparing active polymers and copolymers.

13 Claims, 1 Drawing Figure

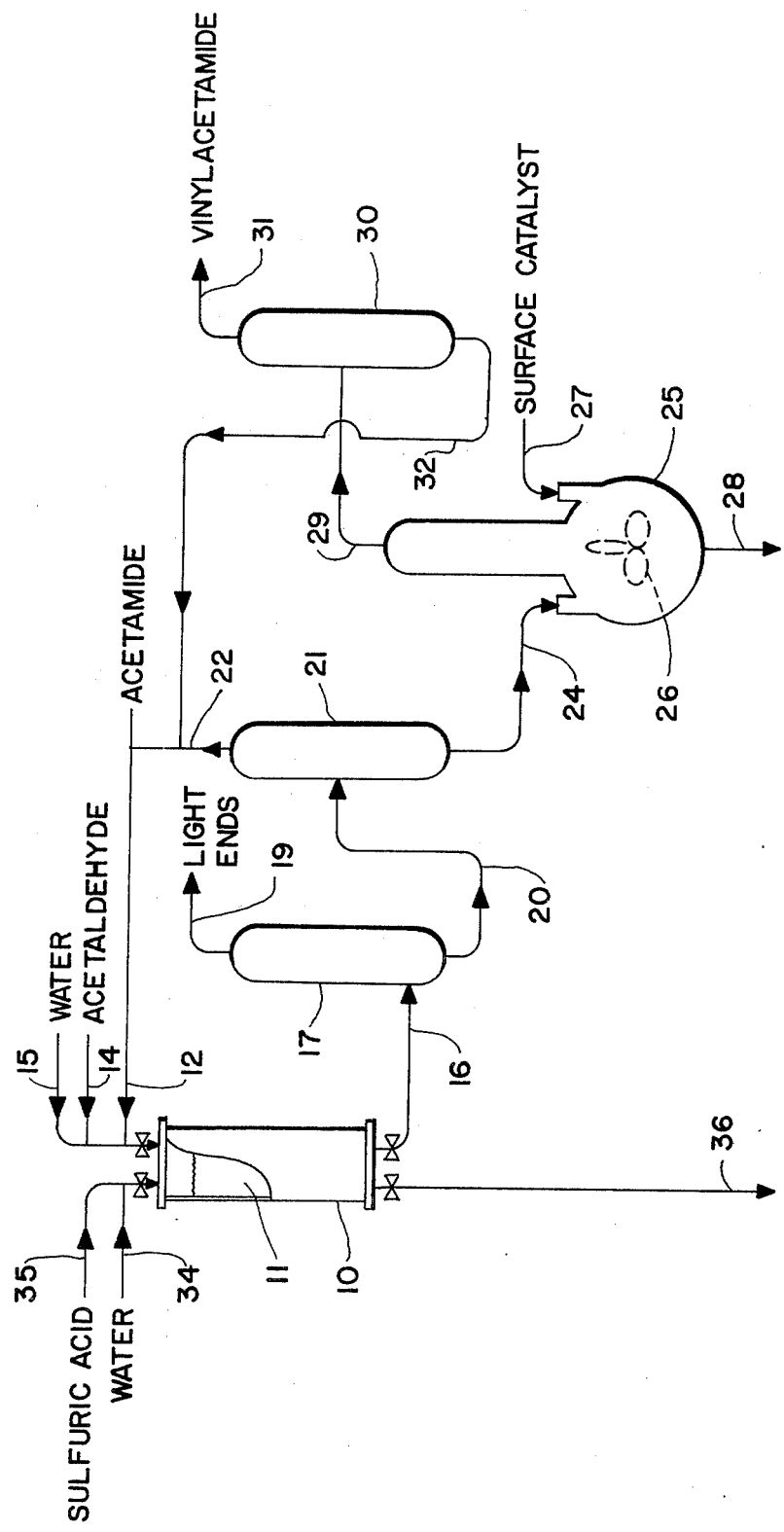

PROCESS FOR PREPARING ETHYLIDENE-BIS-ACETAMIDE

BACKGROUND OF THE INVENTION

1. Field of the Invention

This invention concerns a process for preparing ethylidene-bis-acetamide from acetaldehyde and acetamide and optionally thereafter converging the ethylidene-bis-acetamide to vinylacetamide.

2. The Prior Art

U.S. Pat. No. 4,018,826, issued on Apr. 19, 1977, to my coworkers, Richard Gless, Daniel J. Dawson, and Robert E. Wingard, discloses a process for preparing the useful active polymer poly(vinylamine) wherein acetaldehyde and acetamide are formed into ethylidene-bis-acetamide which is then cracked to yield vinylacetamide which is polymerized and hydrolyzed to poly(vinylamine). In the reference patent acetaldehyde and acetamide are reacted in liquid phase in the presence of a liquid strong mineral acid. While this method is effective, it has the failings of not always giving reproducible color and quality product and of requiring laborious and expensive separation of the ethylidene-bis-acetamide from the liquid acid phase. Other references to the condensation reaction of acetaldehyde and acetamide in the prior art include V. v.Richter, *Ber.* 5, 477 (1877); W. Noyes et al., *J. Am. Chem. Soc.*, 55, 3493 (1933) and Ben Ishai et al., *Tetrahedron Letters*, 50, 4523 (1965). Also, a general review article on the condensation of aldehydes and amides may be found at *Organic Reactions*, 14, 52 (1965). The present invention is an improved method for carrying out this reaction of acetamide and acetaldehyde.

STATEMENT OF THE INVENTION

It has now been discovered that the condensation of acetamide with acetaldehyde to form ethylidene-bis-acetamide proceeds with improved efficiency when it is carried out using a solid cation exchange resin as catalyst in place of the liquid strong mineral acid. In accord with this invention ethylidene-bis-acetamide is formed by contacting a liquid admixture of acetaldehyde and acetamide, generally in the mole ratio of about two moles of acetamide per mole of acetaldehyde, and optionally in the presence of water, with a solid cation exchange resin. This contacting is carried out at ambient to moderate temperature, such as 10°–110° C., and for a time defined in a batch mode as for from 5 to 60 minutes, and defined in a continuous mode as a weight hourly space velocity of 0.01 to 2 kg of acetaldehyde per kilogram of resin per hour. Optionally, the ethylidene-bis-acetamide containing product which results is treated to remove water and excess acetamide and then cracked with heat and optionally an inorganic surface catalyst to yield vinylacetamide.

DETAILED DESCRIPTION OF THE INVENTION

The invention may be described with reference to the accompanying drawing. In the sole FIGURE a schematic flow diagram of one embodiment of the process of this invention is depicted. Elongated cylindrical reactor 10 is charged with a bed 11 of particulate sulfonated divinylbenzene-cross-linked polystyrene ion exchange resin. This resin is in the protonated (H+) form. While the resin is shown in a fixed bed configuration in the FIGURE, it will be appreciated that it could be in a stirred or fluidized bed configuration as well. Acetamide, acetaldehyde and water, in appropriate ratios, are continuously fed to the top of the resin bed via valved conduits 12, 14 and 15, respectively. The rate of reactant feed is regulated to provide a WHSV of from 0.01 to 2 kg of acetaldehyde/kg of resin/hour. Heat can be added to or removed from reactor 10 by means not shown as needed to control the reaction remperature, preferably between about 50° C. and about 110° C. A crude reaction product composed principally of water, unreacted acetaldehyde and acetamide, and ethylidine-bis-acetamide is continuously removed via valved conduit 16 to stripper 17. In stripper 17, a reduced pressure, generally from 600 to 200 mm of mercury absolute, is applied along with heat to maintain a bottom temperature of from about 70° to 150° C. Light materials are stripped overhead and are removed via conduit 19. These light materials include principally unreacted acetaldehyde, water and some acetamide. These light materials are condensed and may be discarded or treated to recover acetaldehyde, acetamide and water for recycle. A bottoms product, composed primarily of ethylidene-bis-acetamide and acetamide, is removed via conduit 20 to distillation column 21. Acetamide is taken overhead in column 21, condensed by means not shown, and removed via conduit 22, preferably to recycle to acetamide feed conduit 12. The bottoms product of column 21, composed of ethylidene-bis-acetamide and acetamide, is removed via conduit 24 to cracker 25. Cracker 25 is optionally equipped with agitator 26 and heating means not shown. A surface catalyst, very suitably glass powder, diatomaceous earth or a similar high surface area silicon or oxidic insoluble solid surface catalyst is charged to cracket 25 via conduit 27. The mixture of ethylidene-bis-acetamide and catalyst is heated (and optionally stirred). The cracker conditions are an absolute pressure of 30 to 100 mm of mercury and a temperature of 175° to 220° C. Under these conditions the ethylidene-bis-acetamide cracks to give vinylacetamide and acetamide. These products, as well as any residual acetamide present in the column 21 bottoms, are volatilized at the conditions of cracker 25 and are removed as an overhead via conduit 29. This overhead fraction is condensed and fed to distillation column 30. In column 30 the more volatile vinylacetamide is taken overhead, condensed, and removed as a liquid via conduit 31. Column 30 is generally operated at conditions such as a bottoms temperature of 130° to 180° C. and an absolute pressure of 30 to 100 mm of mercury. A bottoms fraction composed principally of acetamide is isolated and removed via conduit 32. Preferably, as is shown, this acetamide is recycled to feed line 12. There is real reason to remove and recover acetamide in two stages—one before and one after cracking. By so doing, the temperature in the cracker can be held at a high enough level to permit efficient cracking. Cracker 25 is equipped with bottoms take off 28 through which spent catalyst and heavy end byproducts can be withdrawn.

As the continuous process shown in the FIGURE is run, the resin bed 11 gradually becomes contaminated and deactivated by ammonium salts which are normally present in the aqueous acetamide feed. Periodically, feed conduits 12, 14 and 15 are blocked off. The valve on product conduit 16 is closed and an aqueous mixture of acid, such as sulfuric acid, is charged to the reactor via lines 35 and 34, respectively. This removes the deactivating salts and returns the resin bed to activity. The acid-water mixture is removed via conduit 36 and the bed is rinsed with water via conduit 34 which rinse is also removed via conduit 36.

The reactants, catalysts and conditions employed in this invention may also be described as follows:

The Reactants.

The reactants in this process are acetamide and acetaldehyde. They react as follows:

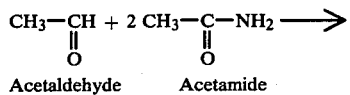
Acetaldehyde    Acetamide

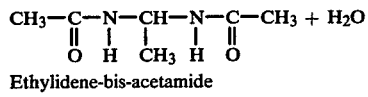
Ethylidene-bis-acetamide

As can be seen, stoichiometrically, acetaldehyde and acetamide are employed in a molar ratio of 1:2. Generally, however, it is preferred to use somewhat of an excess of acetamide. Major excesses do not appear to offer benefit, so suitably the ratio is controlled from 1:2 to about 1:4 inclusive, with ratios of from about 1:2 to 1:3 being more preferred. Reaction will occur at ratios outside these ranges, such as below 1:2 or above 1:4 but such conditions are not seen to offer any advantage and present the obvious disadvantage of involving large excess of one reactant or the other which must be recovered and recycled.

Other materials may optionally be present in the reaction mixture. One material is very suitably present—water. Water does not interfere with the reaction and increases the reaction liquid volume and permits the reaction liquid's easier contacting with the resin. From 0 to about 500% by weight (basis acetaldehyde plus acetamide) of water may be present in the reaction mixture with amounts of from about 0% to 200%, on the same weight basis, being preferred.

The Ion Exchange Resin

The ion exchange resin employed in the present process is solid and insoluble in the reaction medium and the reactants and products. It may be macroporous. It is a cation exchange resin.

Cation exchange resins contain acidic groups such as carboxylic acid and sulfonic acid groups or radicals. They are not necessarily acidic in the sense of giving to water in contact therewith a pH value of less than 7. Examples of suitable resins include resins derived from monohydric and polyhydric phenols and aldehydes which are further modified by reaction with sulfurous acid, sulfites and sulfur dioxide and sulfonated polystyrene which is crosslinked such as with divinylbenzene. Such materials are available commercially from Dow Chemical Company under trademarks Dowex 50W-×8, 10, 12 and 16 and Dowex MSC-1; from Rohm and Haas Company under trademarks Amberlite 200, Amberlite IR 118, 120, 122, and Amberlite IRC 50; from Diamond Shamrock as Duolite C-3, C-20, C-20×10, CC-33 and C-25D; from Permutit Company (England) as Zeocarb 225, 215 and 226; from Permutit Company (USA) as Permutit Q, Q 110, and Q 210; and from BioRad Laboratories as BioRex 40 and 70 and as AG-50-×8 and AG-MP-50. These materials are representative of other comparable commercial or prepared ion exchange resins. A mixture of two or more resins could be used as well.

Preferred, because of ready availability, are the sulfonated divinylbenzene-crosslinked polystyrenes. The resins should be employed in a protonated state, that is in their H+ form. This form is obtained by contacting the resin with aqueous mineral acid, such as aqueous $H_2SO_4$, HCl, HBr, $HNO_3$ or the like prior to use. This acid treatment can also serve to regenerate an ion exchange resin which has become deactivated. This deactivation can occur when ammonium ions which generally are present in the aqueous acetamide-acetaldehyde feed displace the hydrogen ions or resin. The acid treatment may be carried out at a temperature of 10° to 100° C. and, preferably 20° to 50° C., and for a time of 10 minutes to 24 hours, preferably 1 hour to 4 hours. The acid is generally dilute with concentrations of from 0.1 to 6 molar in water being employed with at least one mole of acid per mole of protonated sites desired being employed. Following the acid treatment, the resin may suitably be rinsed with water to remove residual acid.

The Reaction Conditions

The contacting of the reactants with the ion exchange resin may be carried out in a continuous or a batch mode. In the continuous mode, the reactants are fed in the desired ratio to a reaction zone containing the ion exchange resin. The resin may be in a fixed bed, stirred or fluidized bed configuration. The reaction products are continuously withdrawn from the reaction zone. The rate at which the reactants are fed to the reaction zone is expressed in terms of the weight hourly space velocity (WHSV) of acetaldehyde passed over or contacted with the ion exchange resin in $$\frac{\text{Kg of acetaldehyde}}{\text{Kg of ion exchange resin} \cdot \text{hour}}.$$

WHSVs of from 0.01 to 2 kg/kg hour are usefully employed with WHSVs of from 0.05 to 1 kg/kg hour being preferred. In a batch mode, it is suitable to react from about 0.01 to about 10 kg of acetaldehyde per kg of resin and to employ reaction times of from about 0.25 hour to about 24 hours. Preferably, about 0.05 to about 0.50 kg of acetaldehyde are used per kg of resin with times of from about 0.5 hours to about 24 hours. Most preferred batch conditions include 0.1 to 0.25 kg of acetaldehyde per kg of resin and a time of 1 hour to 6 hours. In either the batch or the continuous mode, the resin is usually employed in a particulate form.

The reaction is generally carried out at moderate to elevated temperature. The reaction is exothermic so that room temperature feedstocks can result in a reaction zone temperature of from about 25° to about 50° C. Higher temperatures, such as 50° to 125° C., can be employed, if desired. Preferred temperatures are from 25° C. to 110° C. with 35° C. to 100° C. being the most preferred temperature range. In view of the relatively low atmospheric boiling point of the acetaldehyde reactant (20° C.), it may be desirable to employ a superatmospheric pressure. The reaction is preferably carried out as a liquid-solid reaction and pressures to maintain the acetaldehyde in liquid phase, such as pressures of from 1 to 10 atmospheres, preferably 1 to 5 atmospheres, are employed.

Following reaction, the resin and the reaction products are separated. Since the resin is solid and the reaction product is liquid, this can be simply effected. In a continuous reaction mode, the reaction product can be drawn off through a filter, settling basin or the like solid-liquid separation means. In a batch mode, a similar solid-liquid separation step can be employed to effect isolation of the crude reaction product from the solid resin.

The resin-free crude reaction product has water, ethylidene-bis-acetamide, and unreacted acetamide and acetaldehyde as its principal components. It also likely contains minor amounts of byproducts. These byproducts do not interfere with or are removed in later steps and thus are not of major interest. The crude reaction product may be worked up such as by crystallization, precipitation or the like processes to yield the desired ethylidene-bis-acetamide product in a pure form. The ethylene-bis-acetamide also may be used in a semi-pure form. It has been found that the cracking of the ethylidene-bis-acetamide to acetamide and vinylacetamide proceeds well if the water and acetaldehyde present in the crude feed are removed prior to cracking. Also, it is of advantage to remove part of the residual acetamide from the crude feed as well. Acetamide, acetaldehyde and water are all more volatile than ethylidene-bis-acetamide so they can be easily removed overhead by distillation in either one stage, two (as shown in the FIGURE) or more. The bottom product of the distillation, or like process, is composed of ethylidene-bis-acetamide and generally some acetamide.

The bottoms product containing ethylidene-bis-acetamide is thermally decomposed (cracked) to vinylacetamide. This cracking can be carried out thermally, such as by heating the ethylidene-bis-acetamide to about 150° C. to 250° C. for from 0.2 to 5 hours, but preferably is carried out catalytically. The use of a catalyst enables the cracking temperature to be lowered into the range of from 70° C. to 200° C. Suitable catalysts include high surface area inorganic solid materials, preferably of a silicous or oxidic nature. As a general rule, nonacidic catalysts give best results. (A nonacidic catalyst is one which by art-known tests, such as Hammett indicators, gives a nonacidic reading.) Typical useful catalysts include silicous catalysts such as diatomaceous earth, fumed silica, chopped glass fiber, powdered glass, silica gel, and fine sand. Acidic materials to be avoided include silica-alumina hydrocarbon cracking catalysts and the like.

These catalysts should be employed in forms having surface areas of at least about 1 m$^2$/g, preferably with surface areas of from about 10 m$^2$/g to about 400 m$^2$/g. They may be added to the reaction mixture as powders or pellets or could be employed as a bed through which the reaction mixture is gradually passed. Catalysts which give excellent results and are preferred include diatomaceous earth of surface area 5 m$^2$/g to 20 m$^2$/g, marketed under the trade name "Celite," and glass wool of surface area 0.1 m$^2$/g to 1.0 m$^2$/g. Suitable reaction times for the catalytic cracking step are from 0.2 hours to about 6 hours.

The vinylacetamide which is formed in this reaction step is more volatile than the ethylidene-bis-acetamide feed material. It is desirable to remove it by volatilization from the reaction mixture as it is formed. This may be done by pulling a vacuum on the reaction vessel during reaction. Vacuums of from about 10 mm Hg to about 100 mm Hg are suitable to effect volatilization of the vinylacetamide at the cracking reaction temperatures. Residual acetamide volatilized along with the vinylacetamide may undergo purification treatment to remove acetamide. This treatment may take the form of fractional crystallization, distillation, or passage through a bed of resin of a cation exchange type in a liquid reaction medium using a free-radical initiator catalyst. There are two classes of suitable liquid media. Polar hydrogen bonding liquids, like water and lower alkanols, are suitable and function as solvents for the monomer and the polymer product. Non-polar liquids, such as hydrocarbons, ethers, and ketones, are also suitable, functioning as monomer solvents, but not as solvents for the polymer, such that the polymer forms a second phase. Lower alkanols of from 1 to 5 carbons such as methanol, isopropanol, n-butanol and the like, are preferred media, with isopropanol being most preferred.

The amount of reaction media is generally selected to provide a concentration of vinylacetamide monomer of from about 10% to 50% by weight. Lower concentrations could be employed, but are not seen to offer any significant advantage.

A free-radical initiator is employed as catalyst. Suitable catalysts include the organic peroxides and other materials known in the art for this purpose. A commonly available and thus preferred catalyst is AIBN, 2,2;-azobis(2-methyl-propionitrile). The amount of catalyst is not critical. Generally, amounts of from 0.1 gram to 20 grams of catalyst per 100 grams of vinylacetamide is employed with additions of from 1 to 10 grams of catalyst per 100 grams of vinylacetamide being preferred.

The polymerization is carried out at a moderately elevated temperature such as from about 25° C. to about 125° C., with temperatures of from 50° C. to 110° C. being preferred. The polymerization requires from about 4 to 8 hours to complete, depending upon the exact temperature, catalyst, and monomer concentration employed. Generally, the reaction will be monitored by NMR or gas chromatography for unreacted monomer and continued until no significant monomer remains, for example, less than 5%, preferably less than 1%. Reaction medium is then removed and the polymer is recovered by precipitation in a non-solvent. Typical non-solvents include nonpolar organic liquids such as ketones, ethers and hydrocarbons. Suitable non-solvents include acetone, methylethylketone, methylisobutylketone, diethylether, diisopropylether, hexane, cyclohexane, n-pentane, benzene, and the like.

Following precipitation, the polymer product may be recovered, washed, and optionally dried.

The poly(vinylacetamide) product may be hydrolyzed to poly(vinylamine) salt. This hydrolysis is suitably carried out in water in the presence of a strong acid. At least one equivalent of acid per equivalent of poly(vinylacetamide) should be used, such as from 1.05 to 3 equivalents of acid per equivalent of polymer. Too great an excess of acid can cause the hydrolysis product to precipitate prematurely. Suitable acids include, for example, hydrochloric, sulfuric, p-toluene sulfonic, trifluoroacetic and hydrobromic acids, with hydrochloric acid being preferred.

This hydrolysis is carried out at elevated temperatures such as at the reflux temperature of the solution (110° C.) or temperatures in the range of from about 60° C. to 175° C. and, depending upon the temperature, requires from about 1 hour to about 36 hours, preferably 3 hours to 12 hours, to complete.

Following hydrolysis, the polymer salt can be recovered by further acidifying to cause it to precipitate. This may be carried out by adding additional acid to a concentration of 1 to 3 normal, cooling, and isolating the precipitating polymer. The precipitated polymer initially is a gum, but, upon drying, forms a granular solid of poly(vinylamine) salt, such as the hydrochloride or the like. This product is a linear repeating polymer of the formula

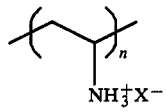

wherein n is 50 to 10,000 so as to provide a molecular weight of from about 4,000 to 800,000 and X⁻ is the anion corresponding to the acid employed in the hydrolysis.

The process may be halted at this point, yielding as its product poly(vinylamine) salt. It also may be carried further, such as to form the free amine. This conversion may be effected by contacting the salt with an aqueous base such as an alkali metal or alkaline earth metal oxide or hydroxide, at a pH of 10 or greater. Typical useful bases include sodium hydroxide and potassium hydroxide. Other basic materials may be used as well, but are not as advantageous costwise. This neutralization may be carried out at temperatures in the range of 15°–50° C. such as at room temperature. This yields the polymeric free amine which may be isolated and dried, if desired. The polyvinyl amine product is a linear polymer. It is water-soluble and has a formula

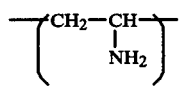

wherein n has a value of from 50 to 10,000 such that the polymer has a molecular weight of from about 2,000 to about 450,000.

One excellent use of the polymeric amine is in the manufacture of polymeric azo and non-azo colorants with the amine functionalities being useful for attaching the chromophoric groups to the polymer backbone. This use is fully described in U.S. Pat. No. 4,018,826 of Gless et al. and application 638,731 of Wingard et al. which patent and application are herein incorporated by reference.

The process of this invention will be further described by the following examples. These are presented solely to illustrate and embody the invention and are not to be construed as limiting the invention's scope.

EXAMPLE I

Into a column (2.5×40 cm) is placed 200 g of particulate porous cation exchange resin made up of sulfonated DVB-crosslinked polystyrene (available commercially as DOWEX 50×8 resin from Dow Chemical Company). This resin is in a protonated form. The resin bed is filled with water to start. Then, a feed mixture of 137 g of acetaldehyde, 390 g of acetamide and 600 ml of water is prepared. This feed mixture is passed over the bed of resin in the column. Water, 80 ml, is removed as initial effluent from the column and discarded. Over a 67 minute period, 180 ml of initial reaction product water is collected. Then, over 306 minutes, 660 ml of crude product are taken off. The initial reaction product (180 ml) is then refed and over 57 minutes an additional 300 ml of reaction product is collected. This reaction product contains ethylidene-bis-acetamide, acetamide, acetaldehyde and water as major components. A portion of the reaction product (that portion collected between 250 minutes and 320 minutes) is placed in a five liter stirred flask having a valved bottom opening. The pressure on the flask is set at 400–500 mm Hg absolute and the internal temperature of the flask is brought to about 100°–120° C. with stirring over a 30 minute period. Water and acetaldehyde are taken overhead and condensed. Heating is continued to an internal temperature of 173° C. for an additional 40 minutes while bringing the pressure down to 55 mm. This causes acetamide to be taken overhead. The remaining ethylidene-bis-acetamide and acetamide is withdrawn as a melt via the bottom opening and passed to a two-liter stirred flask containing 44 g of powdered pyrex glass and 33 g of CaCO₃. The flask is heated to about 180° C., a vacuum of 35–43 mm absolute is applied. Over a period of 70 minutes, the cracking is carried out. During this period the internal temperature climbs to about 195°–200° C. Vinylacetamide and acetamide are taken overhead and condensed. If desired, the acetamide and vinylacetamide could be separated, such as by distillation. Alternatively, this crude mixture of acetamide and vinylacetamide can be contacted with a free radical polymerization catalyst and optionally a copolymerizate to form a polyvinylacetamide or a vinylacetamide copolymer. This polymerization can be effected in the presence of 1–3% molar of catalyst such as AIBN and a temperature of 60°–90° C. for 100–200 minutes.

EXAMPLE II

The preparation of ethylidene-bis-acetamide depicted in Example I is repeated with several modifications. First, a resin bed is prepared. Six kg of Amberlite IR-120 Plus (a Rohm and Haas sulfonated cross-linked polystyrene resin) is washed with water until its yellow color is essentially gone and then packed into a 12×100 cm column to give a 74 cm deep bed. The column is then treated with 8 liters of 3 N HCl and rinsed with 35–40 liters of water until the pH of the rinse water is above 5.

Seven batches of acetaldehyde-acetamide-water are then made up. Each contains 440 g of acetaldehyde, 1500 g of acetamide and 2 liters of water. This gives an acetamide: acetaldehyde ratio of 2.4:1. The batches are added to the top of the resin bed as follows:

| BATCH NUMBER | TIME OF ADDITION |
| --- | --- |
| 1 | 0 minutes |
| 2 | 21 minutes |
| 3 | 47 minutes |
| 4 | 104 minutes |
| 5 | 145 minutes |
| 6 | 196 minutes |
| 7 | 244 minutes |

The first 3.65 liters of effluent are essentially water and are discarded. Between 311 minutes and 337 minutes, the next 1.8 liters of effluent are refed. The effluent is collected. The collected effluent has acetamide, water and ethylidene-bis-acetamide as its major components and is gradually fed to a 50 liter stirred flask held at 70–80 mm of mercury absolute pressure and 40°–60° C. This causes water and some acetamide to distill overhead where it is collected and removed. Celite ® diatomaceous earth is added (720 g) and the temperature is raised to 200°–210° C. Remaining acetamide distills overhead, and the ethylidene-bis-acetamide cracks to yield vinylacetamide which comes over as well and is recovered. The vinylacetamide so formed can be purified if desired or may be formed into polymers or copolymers in its crude state.

What is claimed is:

1. The process for preparing ethylidene bisacetamide which comprises contacting a liquid admixture comprising acetamide, acetaldehyde and water in an amount of up to 500% by weight inclusive based on the amount of acetaldehyde and acetamide with a solid cation exchange resin in $H^+$ form at a weight hourly space velocity of from about 0.01 to about 2 kilograms of acetaldehyde per kilogram of resin per hour and a temperature of from about 25° C. to about 110° C. thereby forming an ethylidene bis/acetamide-containing reaction product and thereafter separating said reaction product from said cation exchange resin.

2. The process of claim 1 wherein said cation exchange resin is a strong acid cation exchange resin.

3. The process of claim 2 wherein said liquid admixture contains acetaldehyde and acetamide in the molar ratio of 1:2 to 1:4 inclusive.

4. The process of claim 3 wherein said cation exchange resin is a protonated sulfonated divinylbenzene-crosslinked polystyrene.

5. The process of claim 4 wherein said resin is activated and reactivated by contact with mineral acid.

6. The process of claim 5 wherein said process is a continuous process.

7. The process of claim 6 wherein said solid cation exchange resin is in a fixed bed configuration.

8. The process of claim 6 wherein said solid cation exchange resin is in a stirred configuration.

9. The process for preparing ethylidene bisacetamide which comprises contacting a liquid admixture comprising acetamide, acetaldehyde and water in an amount of up to 500% by weight inclusive based on the amount of acetaldehyde and acetamide with a solid cation exchange resin in $H^+$ form for a period of 0.25 hours to 24 hours inclusive at a temperature of from 25° to 110° C. thereby forming an ethylidene bis-acetamide-containing reaction product and thereafter separating said reaction product from said cation exchange resin.

10. The process of claim 9 wherein said cation exchange resin is a strong acid cation exchange resin.

11. The process of claim 9 wherein said liquid admixture contains acetaldehyde and acetamide in the molar ratio of 1:2 to 1:4 inclusive.

12. The process of claim 11 wherein said cation exchange resin is a protonated sulfonated divinylbenzene-crosslinked polystyrene.

13. The process of claim 12 wherein said cation exchange resin is in a stirred bed configuration.

* * * * *